US009176641B1

(12) United States Patent
Dixon, III et al.

(10) Patent No.: US 9,176,641 B1
(45) Date of Patent: Nov. 3, 2015

(54) RADIAL VIEW FOR DISPLAY OF TEMPORAL DATA

(71) Applicant: ALLSCRIPTS SOFTWARE, LLC, Raleigh, NC (US)

(72) Inventors: George F. Dixon, III, Philadelphia, PA (US); David Thomas Windell, Raleigh, NC (US); Carin Mann, Malvern, PA (US); Scott Bower, Raleigh, NC (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 131 days.

(21) Appl. No.: 13/831,244

(22) Filed: Mar. 14, 2013

Related U.S. Application Data

(60) Provisional application No. 61/683,106, filed on Aug. 14, 2012.

(51) Int. Cl.
*G06F 3/048* (2013.01)
*G06F 3/0481* (2013.01)
*G06F 19/00* (2011.01)
*A61B 5/00* (2006.01)
*G06F 3/01* (2006.01)

(52) U.S. Cl.
CPC .............. *G06F 3/04817* (2013.01); *A61B 5/00* (2013.01); *G06F 19/324* (2013.01)

(58) Field of Classification Search
CPC ..... G06F 3/0481; G06F 3/04817; G06F 1/14; G06F 15/0266; G06T 11/206; G04F 1/005
USPC ........................... 715/730, 834, 844; 345/440
See application file for complete search history.

(56) References Cited

U.S. PATENT DOCUMENTS

| | | | |
|---|---|---|---|
| 2008/0081594 A1 | 4/2008 | Lee | |
| 2009/0125831 A1* | 5/2009 | Dandurand | 715/772 |
| 2010/0083164 A1 | 4/2010 | Martin | |
| 2010/0157742 A1* | 6/2010 | Relyea et al. | 368/28 |
| 2011/0004835 A1 | 1/2011 | Yanchar | |
| 2012/0066629 A1 | 3/2012 | Lee | |
| 2012/0260135 A1* | 10/2012 | Beck et al. | 714/45 |
| 2013/0104077 A1* | 4/2013 | Felt | 715/810 |

OTHER PUBLICATIONS

Information Disclosure Statement (IDS) Letter Regarding Copending Patent Application dated Aug. 10, 2015.

* cited by examiner

*Primary Examiner* — Amy Ng
*Assistant Examiner* — Seth A Silverman
(74) *Attorney, Agent, or Firm* — Tillman Wright, PLLC; Chad D. Tillman; Jeremy C. Doerre

(57) ABSTRACT

A method for displaying temporal data via a graphical user interface in a manner designed to facilitate easy review and comprehension includes displaying, to a user via a display screen of an electronic device, a radial graphical user interface element configured to display the return of results, the radial graphical user interface element displaying a plurality of icons positioned in one or more circumferential rings of the radial graphical user interface element, the icons representing abnormal readings or measurements having an associated time falling over a displayed twelve hour period, and an indication, in a central area of the radial graphical user interface element, of a total number of abnormal readings or measurements falling over a certain period; wherein each of the icons is displayed on the radial graphical user interface element in a position corresponding to the time associated with the icon it represents.

20 Claims, 6 Drawing Sheets

RADIAL VIEW FOR DISPLAY OF TEMPORAL DATA

CROSS-REFERENCE TO RELATED APPLICATION

The present application is a U.S. nonprovisional patent application of, and claims priority under 35 U.S.C. §119(e) to, U.S. provisional patent application Ser. No. 61/683,106, filed Aug. 14, 2012.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

COMPUTER PROGRAM LISTING

Submitted concurrently herewith via the USPTO's electronic filing system, and incorporated herein by reference, are computer program files including instructions, routines, and/or other contents of several computer program. A table setting forth the name and size of files included in the computer program listing is included below.

| File Name | Creation Date | File Size (bytes) |
|---|---|---|
| readme.txt | Aug. 14, 2012 18:06 | 2745 |
| ASCIFY.txt | Aug. 14, 2012 13:18 | 37473 |
| main-zip1.txt | Aug. 14, 2012 13:22 | 22478848 |
| main-zip2.txt | Aug. 14, 2012 13:22 | 22478848 |
| main-zip3.txt | Aug. 14, 2012 13:22 | 22478848 |
| main-zip4.txt | Aug. 14, 2012 13:22 | 22478848 |
| main-zip5.txt | Aug. 14, 2012 13:22 | 22478848 |
| main-zip6.txt | Aug. 14, 2012 13:22 | 22478848 |
| main-zip7.txt | Aug. 14, 2012 13:22 | 22478848 |
| main-zip8.txt | Aug. 14, 2012 13:22 | 8867045 |

One of these files, "readme.txt", contains instructions for extracting information from other of the files. These other files are compressed binary files that have been converted to ascii format. These files can be converted back to a compressed .zip archive utilizing an assembly conversion program source code for which is contained in "ascify.txt". The readme file includes instructions for compiling and running this conversion program, and instructions for converting the other text files to compressed, binary files, as well as instructions for recreating a directory structure for these compressed files.

Some of these compressed, binary files include source code written in C Sharp that can be compiled utilizing Microsoft Visual Studio 2008. The target environment for implementations utilizing such source code is 32-bit or 64-bit Windows XP, Vista, or 7.

BACKGROUND OF THE INVENTION

The present invention generally relates to the visual presentation of data. Data, and in particular temporal data, such as task data or event data, is commonly displayed in a visual format for viewing. Such a visual format may include, for example, a scheduled view or a horizontal display. However, for example with respect to tasks, if there are a lot of tasks due to be done across a span of hours, viewing this data can involve a lot of scrolling and it can be difficult to visualize how time should be distributed throughout the time interval.

A need exists for improvement in the visual presentation of data. This, and other needs, are addressed by one or more aspects of the present invention.

SUMMARY OF THE INVENTION

The present invention includes many aspects and features. Moreover, while many aspects and features relate to, and are described in, the context of healthcare, the present invention is not limited to use only in this context, as will become apparent from the following summaries and detailed descriptions of aspects, features, and one or more embodiments of the present invention.

Accordingly, one aspect of the present invention relates to a graphical user interface configured to display temporal data, such as tasks, events, or alerts, in a clock view designed to facilitate easy review and comprehension.

In a feature of this aspect, the clock view is divided up into hour intervals for twelve hours at a time.

In a feature of this aspect, the clock view is further configured to change coloring based on a time of day, so as to allow for easy differentiation between day time and night time clock views.

In a feature of this aspect, the clock view can include different rings for display of different types or groups of temporal data.

In a feature of this aspect, the method comprises displaying the radial graphical user interface element as part of a nursing dashboard.

In a feature of this aspect, the method additionally comprises displaying, to the user via the display screen of an electronic device, a second radial graphical user interface element configured for use as a medication clock, the second radial graphical user interface element displaying a plurality of icons representing tasks having an associated time falling over a displayed twelve hour period.

In a feature of this aspect, the display screen comprises a touchscreen.

In a feature of this aspect, the display screen comprises a monitor.

In a feature of this aspect, the electronic device comprises a desktop computer.

In a feature of this aspect, the electronic device comprises a laptop.

In a feature of this aspect, the electronic device comprises a workstation.

In a feature of this aspect, the display screen comprises a television.

In a feature of this aspect, the electronic device comprises a mobile device.

In a feature of this aspect, the electronic device comprises a smart phone.

Another aspect relates to a method for displaying temporal data via a graphical user interface in a manner designed to facilitate easy review and comprehension, the method comprising after midnight, displaying, to a user via a display screen of an electronic device, a first radial graphical user interface element comprising a plurality of icons representing tasks having an associated time falling between midnight and noon; after noon, displaying, to a user via a display screen of an electronic device, a second radial graphical user interface element comprising a plurality of icons representing tasks having an associated time falling between noon and midnight; wherein each of the icons is displayed on its respective radial graphical user interface element in a position corresponding to the time associated with the icon it represents.

In a feature of this aspect, display screen comprises a touchscreen.

In a feature of this aspect, the display screen comprises a monitor.

In a feature of this aspect, the electronic device comprises a desktop computer.

In a feature of this aspect, the electronic device comprises a laptop.

In a feature of this aspect, the electronic device comprises a workstation.

In a feature of this aspect, the electronic device comprises a mobile device.

In a feature of this aspect, the electronic device comprises a smart phone.

Another aspect relates to a computer readable medium containing computer executable instructions for performing a method for displaying temporal data via a graphical user interface in a manner designed to facilitate easy review and comprehension, the method comprising after midnight, displaying, to a user via a display screen of an electronic device, a first radial graphical user interface element comprising a plurality of icons representing tasks having an associated time falling between midnight and noon; after noon, displaying, to a user via a display screen of an electronic device, a second radial graphical user interface element comprising a plurality of icons representing tasks having an associated time falling between noon and midnight; wherein each of the icons is displayed on its respective radial graphical user interface element in a position corresponding to the time associated with the icon it represents.

Another aspect relates to a method for displaying temporal data via a graphical user interface in a manner designed to facilitate easy review and comprehension that includes displaying, to a user via a display screen of an electronic device, a radial graphical user interface element configured to display the return of results, the radial graphical user interface element displaying a plurality of icons positioned in one or more circumferential rings of the radial graphical user interface element, the icons representing abnormal readings or measurements having an associated time falling over a displayed twelve hour period, and an indication, in a central area of the radial graphical user interface element, of a total number of abnormal readings or measurements falling over a certain period; wherein each of the icons is displayed on the radial graphical user interface element in a position corresponding to the time associated with the icon it represents.

In a feature of this aspect, the certain period comprises a day.

In a feature of this aspect, the certain period comprises twelve hours.

In a feature of this aspect, the certain period comprises the displayed twelve hour period.

In a feature of this aspect, the displayed indication comprises a number.

In a feature of this aspect, the method comprises displaying the radial graphical user interface element as part of a nursing dashboard.

In a feature of this aspect, the method additionally comprises displaying, to the user via the display screen of an electronic device, a second radial graphical user interface element configured for use as a medication clock, the second radial graphical user interface element displaying a plurality of icons representing tasks having an associated time falling over a displayed twelve hour period.

In a feature of this aspect, the display screen comprises a touchscreen.

In a feature of this aspect, the display screen comprises a monitor.

In a feature of this aspect, the electronic device comprises a desktop computer.

In a feature of this aspect, the electronic device comprises a laptop.

In a feature of this aspect, the electronic device comprises a workstation.

In a feature of this aspect, the display screen comprises a television.

In a feature of this aspect, the electronic device comprises a mobile device.

In a feature of this aspect, the electronic device comprises a smart phone.

Another aspect relates to a method for displaying temporal data via a graphical user interface in a manner designed to facilitate easy review and comprehension that includes after midnight, displaying, to a user via a display screen of an electronic device, a first radial graphical user interface element comprising a plurality of icons positioned in one or more circumferential rings of the radial graphical user interface element, the icons representing abnormal readings or measurements having an associated time falling between midnight and noon, and an indication, in a central area of the radial graphical user interface element, of a total number of abnormal readings or measurements falling over a first certain period after noon, displaying, to a user via a display screen of an electronic device, a second radial graphical user interface element comprising a plurality of icons positioned in one or more circumferential rings of the radial graphical user interface element, the icons representing abnormal readings or measurements having an associated time falling between noon and midnight, and an indication, in a central area of the radial graphical user interface element, of a total number of abnormal readings or measurements falling over a second certain period wherein each of the icons is displayed on its respective radial graphical user interface element in a position corresponding to the time associated with the icon it represents.

In a feature of this aspect, the first and second certain periods both comprise a day.

In a feature of this aspect, the first certain period comprises the period between midnight and noon, and the second certain period comprises the period between noon and midnight.

In a feature of this aspect, each displayed indication comprises a number.

Another aspect relates to a computer readable medium containing computer executable instructions for performing a method for displaying temporal data via a graphical user interface in a manner designed to facilitate easy review and comprehension, the method comprising displaying, to a user via a display screen of an electronic device, a radial graphical user interface element configured to display the return of results, the radial graphical user interface element displaying a plurality of icons positioned in one or more circumferential rings of the radial graphical user interface element, the icons representing abnormal readings or measurements having an associated time falling over a displayed twelve hour period, and an indication, in a central area of the radial graphical user interface element, of a total number of abnormal readings or measurements falling over a certain period; wherein each of the icons is displayed on the radial graphical user interface element in a position corresponding to the time associated with the icon it represents.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
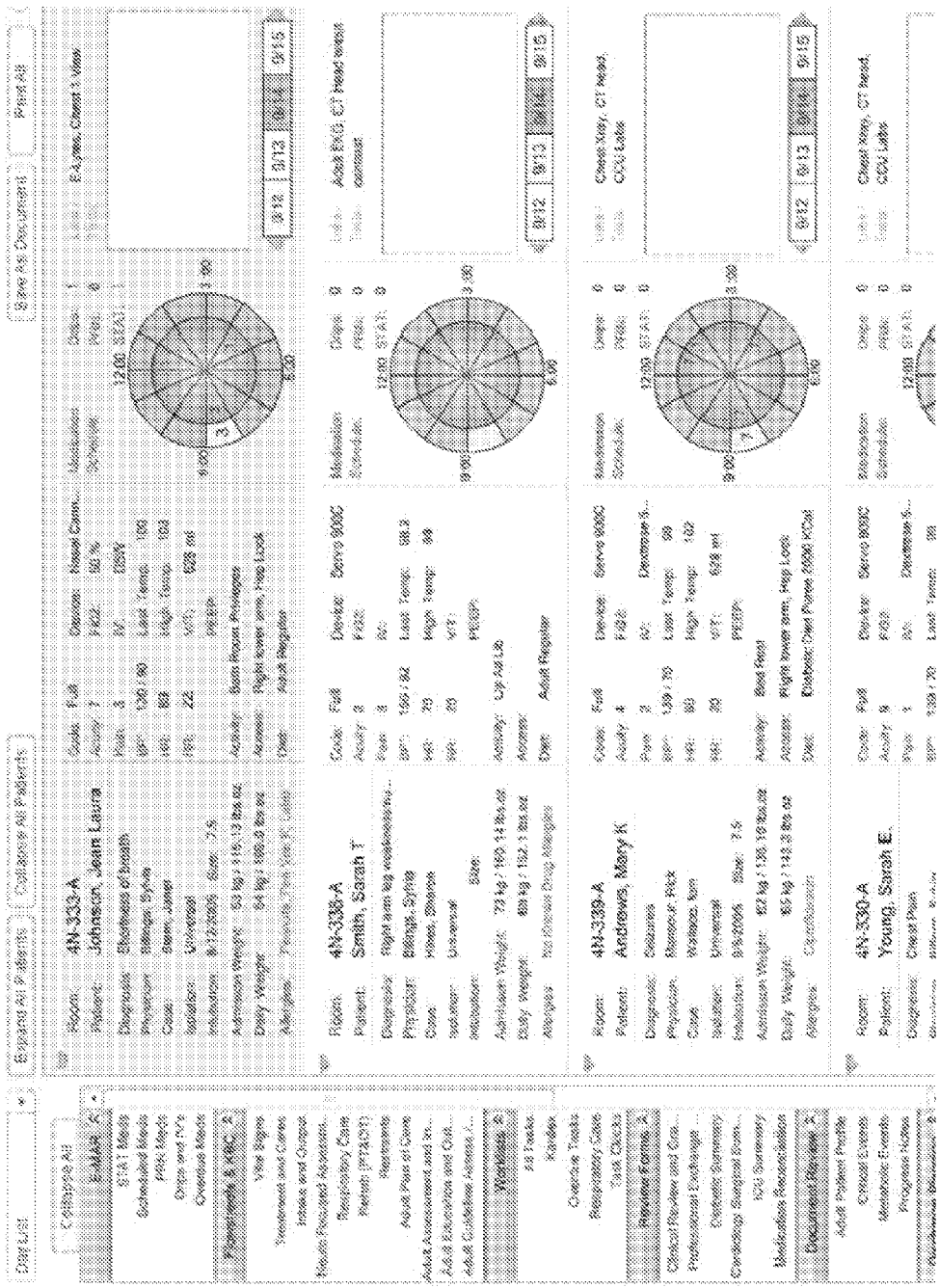
FIG. 1 illustrates the exemplary use of a plurality of radial controls as medication clocks as part of a nursing dashboard that provides an overview of assigned patients.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

An aspect in accordance with a preferred embodiment of the present invention relates to a graphical user interface for displaying temporal data, such as tasks, events, or alerts, in a radial, or clock, view designed to facilitate easy review and comprehension.

For example, in one or more preferred implementations, a radial graphical user interface element, or control, is configured for use as a medication clock. FIG. 1 illustrates exemplary use of a plurality of such controls as medication clocks as part of a nursing dashboard that provides an overview of assigned patients.

Providing medication to a patient is merely one example of a task that could be displayed via such a radial control. In one or more preferred implementations, a clock view of tasks provides a user a high level view of how many tasks are due to be performed by the hour. In some implementations, this is implemented for a subset of tasks, such as medications due or nursing treatments to be given, but in at least some implementations this is expanded to include different tasks. Similarly, in some implementations displayed tasks are all tasks for a single user, person, or entity, while in at least some implementations displayed tasks may be tasks for different users, persons, or entities.

Figure 2:
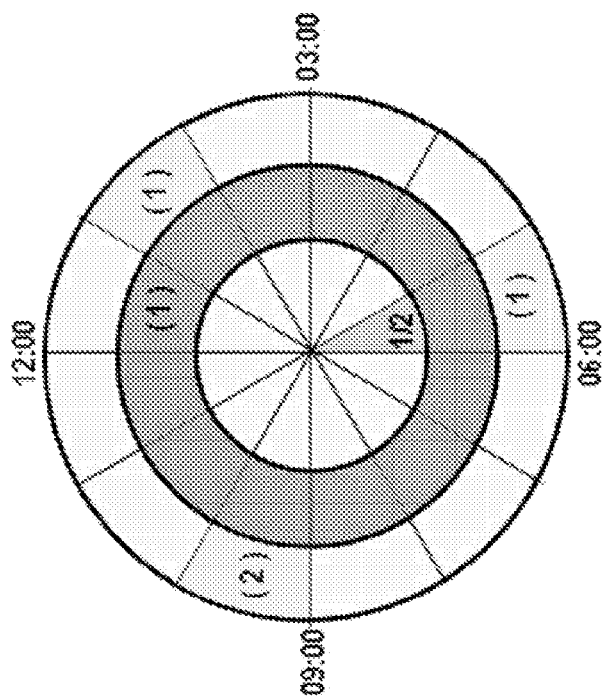
FIGS. 2-5 illustrate exemplary clock views.
Figure 3:
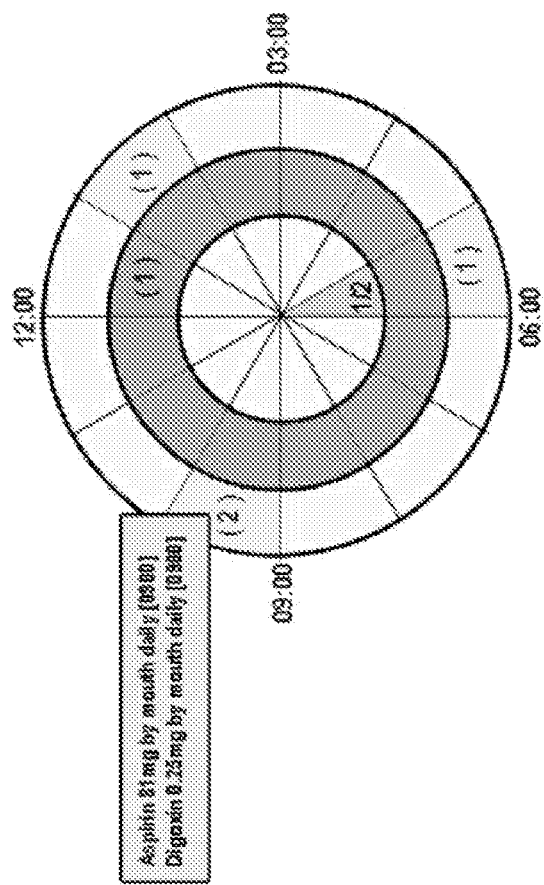
Figure 4:
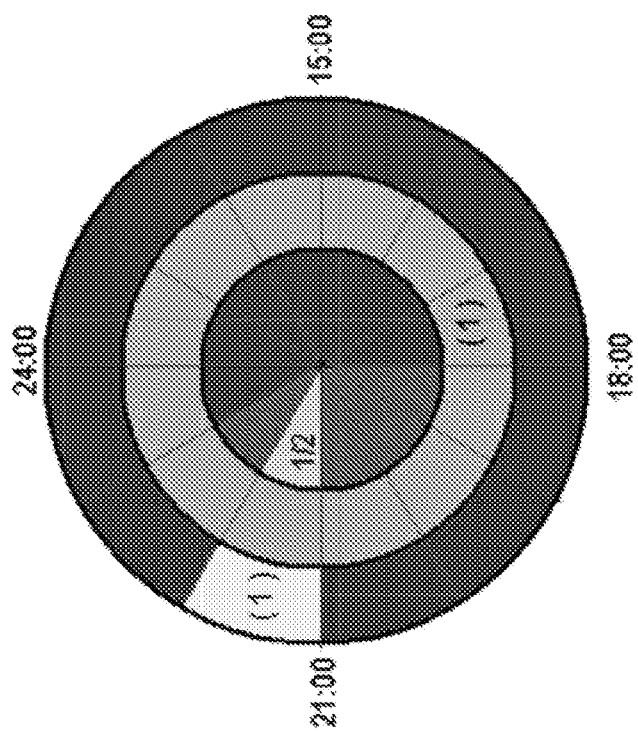
Figure 5:
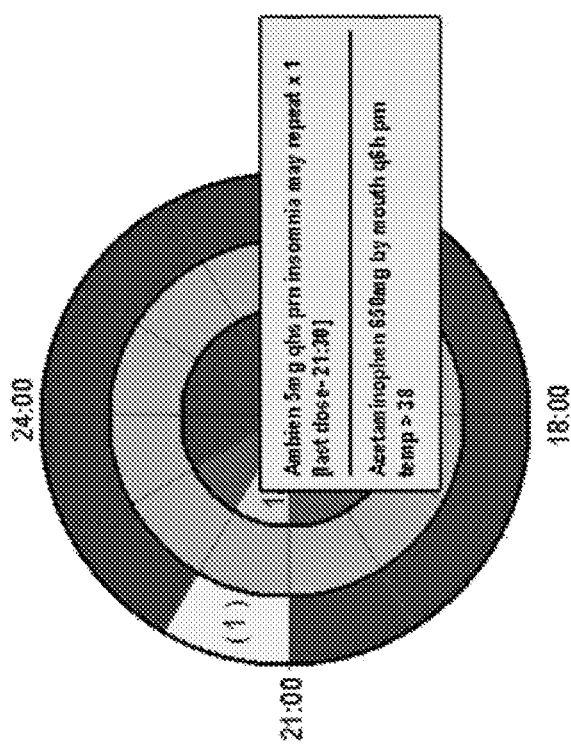

In a preferred implementation, a clock view, or radial control, is divided up into hour intervals for twelve hours at a time, as illustrated in FIG. 2. In some preferred implementations, the radial control is configured such that the control will change based on the time of day. In a preferred implementation, a day time view will display from 0:01-12:00 and have a lighter shading, as illustrated in FIGS. 2-3, while a nighttime view will display from 12:01-24:00 and have a darker shading for easier distinction, as illustrated in FIGS. 4-5. In one or more preferred implementations, day and night styling allows for easy facilitation between shifts and ensures that there is no confusion in what time something is due to be completed.

In one or more preferred implementations, such as those illustrated in FIGS. 2-5, the rings inside a clock view represent different types of tasks. In some implementations, there is one main section, while in other implementations, such as that illustrated in the referenced figures, there are multiple sections.

In one or more preferred implementations, a current hour is highlighted so as to allow a user to see where it is in the current cycle. In some preferred implementations, a radial control is configured to display related tasks, and the number of related tasks is calculated and displays in the section for that task type and the scheduled hour. Preferably, hovering over the indication of the number of tasks gives you a list of tasks to be completed, as illustrated in FIG. 3. In one or more preferred implementations, clicking on one of the tasks effects navigation to the source of the task for task completion.

FIGS. 2-5 specifically illustrate a radial control configured to display tasks associated with medications due for a patient. It will be appreciated that this is only an exemplary implementation, and that aspects and features disclosed herein are applicable in other contexts as well.

In these figures, each number indicates the number of medications due at that specific interval. As illustrated, the radial control includes three rings. The outer ring relates to scheduled medications; the middle ring relates to IVs and drips; and the inner ring relates to PRN medications.

One or more aspects in accordance with a preferred embodiment of the present invention relate to methodologies for using a clock view display. In one or more methodologies, use of a clock view of data allows a user to easily get a sense of when tasks need to be completed and allows the user to plan his or her day around them.

In one or more preferred implementations, a clock view control is used in a larger summary screen.

For example, if a clock view control is utilized to present data related to medications due for a particular patient over a twelve hour shift, this control can be incorporated into a larger patient summary, which would allow a clinician to hand-off or accept the patient for his or her shift and not only see general patient information but also get a sense of what kind of care they will need throughout the shift. Preferably, provision of the ability to navigate to the source of a task allows a user to obtain more detailed information when desired without requiring them to sift through it when it is not desired.

In one or more preferred implementations, a radial control is configured not just for display of tasks, but for display of any type of temporal data, or for another type of temporal data, such as for display of events, alerts, or reminders.

Figure 6:
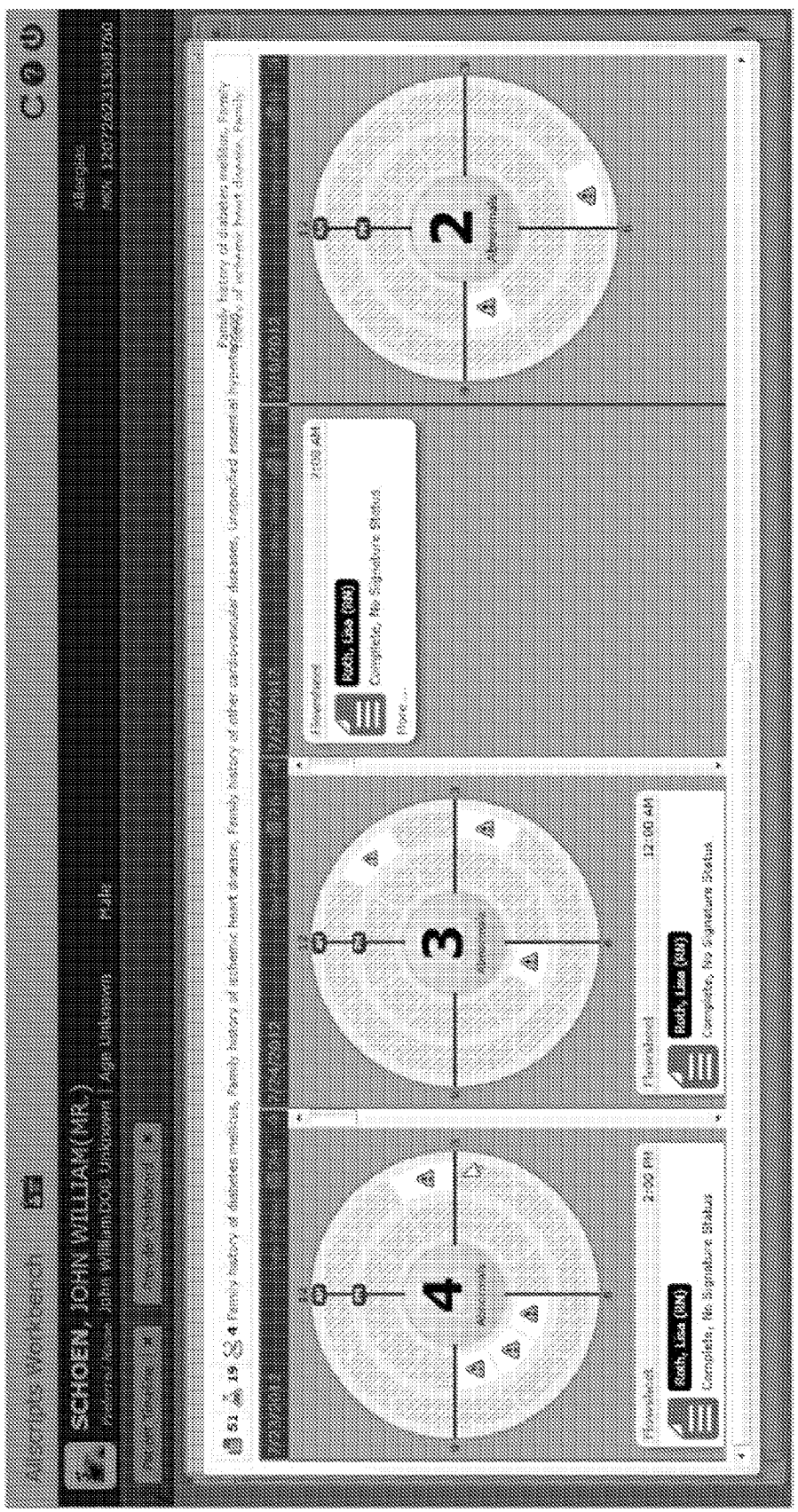
FIG. 6 illustrates use of a clock view display to display data related to abnormal readings or measurements for a patient.

In one or more preferred implementations, rather than displaying tasks in need of completion, a radial control is configured to show the return of results, such as, for example, the returns of laboratory tests, procedures, or other medical or healthcare actions that provide new information to a provider upon their completion. For example, FIG. 6 illustrates use of a clock view display to display data related to abnormal readings or measurements for a patient.

It is believed that, in some implementations, methodologies of use of such differing radial controls by a medical professional differ based on such difference, and the resultant information is used and applied differently by the medical professional. In one or more preferred implementations, different rules and interaction procedures are utilized for abnormal versus normal results. Further, in one or more preferred implementations, a central area of a radial control is utilized for showing daily (or periodic, e.g. 12 hour) totals.

In one or more preferred implementations, a radial control is configured for: the display of medications due for a patient over a shift; the display of nursing treatments due throughout a shift; the display of non-patient specific activities due on a unit or location (such as, for example, blood draws, respiratory therapies, vital signs, etc); the tracking of tasks completed over time by an administrator (in a preferred implementation, for example, an outer ring shows completed items and an inner ring shows outstanding items); the display of patients moving through an office by appointment time (in a preferred implementation, for example, rings represent checked-in, in-room, and seen-by-MD statuses); and/or the distribution of work among clinicians throughout a shift (in a preferred implementation, each ring represents a clinician).

One or more aspects disclosed herein enable clinicians to get a high level view of what is required for their patients to plan accordingly. It is believed that in at least some circumstances this will improve efficiency and ensure that vital tasks are not missed, thereby improving patient care. Notably, however, although described herein largely with respect to a healthcare context, aspects and features disclosed herein are not limited in use to only in such a context. The use of a clock view graphical user interface is contemplated for use in other applications, settings, and contexts as well, such as, for example, in any application for tracking tasks within a shift or hourly time interval.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for displaying temporal data via a graphical user interface of a healthcare software application in a manner designed to facilitate easy review and comprehension, the method comprising:
   (a) displaying, to a user via a display screen of an electronic device,
      (i) a first radial graphical user interface element configured to display a return of results for a particular patient for a first day, the first radial graphical user interface element including
  (A) an outer circumferential ring comprising twelve sections representing the AM hours of the first day,
  (B) an inner circumferential ring comprising twelve sections representing the PM hours of the first day,
  (C) a first plurality of icons each positioned in one of the sections of the inner or outer circumferential rings of the first radial graphical user interface element, the icons representing abnormal readings or measurements having an associated time during the first day, and
  (D) an indication, in a central area of the first radial graphical user interface element, of a total number of abnormal readings or measurements during the first day, and
  (E) wherein each of the icons of the first plurality of icons is displayed on the first radial graphical user interface element in a position corresponding to the time associated with the icon it represents;
(ii) a second radial graphical user interface element configured to display a return of results for the particular patient for a second day, the second radial graphical user interface element including
  (A) an outer circumferential ring comprising twelve sections representing the AM hours of the second day,
  (B) an inner circumferential ring comprising twelve sections representing the PM hours of the second day,
  (C) a second plurality of icons each positioned in one of the sections of the inner or outer circumferential rings of the second radial graphical user interface element, the icons representing abnormal readings or measurements having an associated time during the second day, and
  (D) an indication, in a central area of the second radial graphical user interface element, of a total number of abnormal readings or measurements during the second day, and
  (E) wherein each of the icons of the second plurality of icons is displayed on the second radial graphical user interface element in a position corresponding to the time associated with the icon it represents.

2. The method of claim 1, wherein the displayed indication comprises a number.

3. The method of claim 1, wherein the display screen comprises a touchscreen.

4. The method of claim 1, wherein the display screen comprises a monitor.

5. The method of claim 1, wherein the electronic device comprises a desktop computer.

6. The method of claim 1, wherein the electronic device comprises a laptop.

7. The method of claim 1, wherein the electronic device comprises a workstation.

8. The method of claim 1, wherein the display screen comprises a television.

9. The method of claim 1, wherein the electronic device comprises a mobile device.

10. The method of claim 1, wherein the electronic device comprises a smart phone.

11. A method for displaying temporal data via a graphical user interface of a healthcare software application in a manner designed to facilitate easy review and comprehension, the method comprising:
(a) displaying, to a user via a display screen of an electronic device,
  (i) a first radial graphical user interface element configured to display a return of results for a particular patient for a first day, the first radial graphical user interface element including
    (A) inner and outer circumferential rings each comprising twelve sections, the sections representing the hours of the first day,
    (B) a first plurality of icons each positioned in one of the sections of the inner or outer circumferential rings of the first radial graphical user interface element, the icons representing abnormal readings or measurements having an associated time during the first day, and
    (C) an indication, in a central area of the first radial graphical user interface element, of a total number of abnormal readings or measurements during the first day, and
    (D) wherein each of the icons of the first plurality of icons is displayed on the first radial graphical user interface element in a position corresponding to the time associated with the icon it represents;
  (ii) a second radial graphical user interface element configured to display a return of results for the particular patient for a second day, the second radial graphical user interface element including
    (A) inner and outer circumferential rings each comprising twelve sections, the sections representing the hours of the first day,
    (B) a second plurality of icons each positioned in one of the sections of the inner or outer circumferential rings of the second radial graphical user interface element, the icons representing abnormal readings or measurements having an associated time during the second day, and
    (C) an indication, in a central area of the second radial graphical user interface element, of a total number of abnormal readings or measurements during the second day, and
    (D) wherein each of the icons of the second plurality of icons is displayed on the second radial graphical user interface element in a position corresponding to the time associated with the icon it represents.

12. The method of claim 11, wherein the display screen comprises a touchscreen.

13. The method of claim 11, wherein the display screen comprises a monitor.

14. The method of claim 11, wherein the electronic device comprises a desktop computer.

15. The method of claim 11, wherein the electronic device comprises a laptop.

16. The method of claim 11, wherein the electronic device comprises a workstation.

17. The method of claim 11, wherein the display screen comprises a television.

18. The method of claim 11, wherein the electronic device comprises a mobile device.

19. The method of claim 11, wherein the electronic device comprises a smart phone.

20. One or more non-transitory computer readable media containing computer executable instructions for performing a method for displaying temporal data via a graphical user interface of a healthcare software application in a manner designed to facilitate easy review and comprehension, the method comprising:

(a) displaying, to a user via a display screen of an electronic device,
   (i) a first radial graphical user interface element configured to display a return of results for a particular patient for a first day, the first radial graphical user interface element including
      (A) inner and outer circumferential rings each comprising twelve sections, the sections representing the hours of the first day,
      (B) a first plurality of icons each positioned in one of the sections of the inner or outer circumferential rings of the first radial graphical user interface element, the icons representing abnormal readings or measurements having an associated time during the first day, and
      (C) an indication, in a central area of the first radial graphical user interface element, of a total number of abnormal readings or measurements during the first day, and
      (D) wherein each of the icons of the first plurality of icons is displayed on the first radial graphical user interface element in a position corresponding to the time associated with the icon it represents;
   (ii) a second radial graphical user interface element configured to display a return of results for the particular patient for a second day, the second radial graphical user interface element including
      (A) inner and outer circumferential rings each comprising twelve sections, the sections representing the hours of the first day,
      (B) a second plurality of icons each positioned in one of the sections of the inner or outer circumferential rings of the second radial graphical user interface element, the icons representing abnormal readings or measurements having an associated time during the second day, and
      (C) an indication, in a central area of the second radial graphical user interface element, of a total number of abnormal readings or measurements during the second day, and
      (D) wherein each of the icons of the second plurality of icons is displayed on the second radial graphical user interface element in a position corresponding to the time associated with the icon it represents.

* * * * *